(12) United States Patent
Ludescher et al.

(10) Patent No.: US 9,266,868 B2
(45) Date of Patent: Feb. 23, 2016

(54) CRYSTALLINE FORM OF RIVAROXABAN DIHYDRATE

(75) Inventors: Johannes Ludescher, Kundl (AT); Hubert Sturm, Kundl (AT); Ulrich Griesser, Axams (AT); Robert E. Ziegert-Knepper, Kundl (AT); Arthur Pichler, Kundl (AT); Mairi Haddow, Bristol (GB)

(73) Assignee: SANDOZ AG, Basel (CH)

( * ) Notice: Subject to any disclaimer, the term of this patent is extended or adjusted under 35 U.S.C. 154(b) by 302 days.

(21) Appl. No.: 13/805,462

(22) PCT Filed: Jul. 5, 2011

(86) PCT No.: PCT/EP2011/061283
§ 371 (c)(1),
(2), (4) Date: May 29, 2013

(87) PCT Pub. No.: WO2012/004245
PCT Pub. Date: Jan. 12, 2012

(65) Prior Publication Data
US 2013/0245017 A1 Sep. 19, 2013

(30) Foreign Application Priority Data
Jul. 6, 2010 (EP) .................................. 10168536

(51) Int. Cl.
*C07D 413/12* (2006.01)
*C07D 413/14* (2006.01)

(52) U.S. Cl.
CPC ............ *C07D 413/12* (2013.01); *C07D 413/14* (2013.01)

(58) Field of Classification Search
CPC ............................. C07D 413/12; C07D 413/14
See application file for complete search history.

(56) References Cited

U.S. PATENT DOCUMENTS 8,648,189 B2  2/2014  Sturm

FOREIGN PATENT DOCUMENTS

| WO | 01/47919 | 7/2001 |
| WO | 2004/060887 A1 | 7/2004 |
| WO | 2004/101557 | 11/2004 |
| WO | 2005/060940 A2 | 7/2005 |
| WO | 2005/068456 A1 | 7/2005 |
| WO | 2006/072367 A1 | 7/2006 |
| WO | 2007/039122 A2 | 4/2007 |
| WO | 2007/039132 A1 | 4/2007 |
| WO | 2009/149851 A1 | 12/2009 |

OTHER PUBLICATIONS

International Search Report mailed Aug. 23, 2011 in PCT/EP2011/061283.
CHMP Assessment Report Procedure No. EMEA/H/C/000944, (2008).
J. Mec. Chem. 2005, 48, 5900-5908.
Third party observation filed in corresponding European Patent Application No. 10168536.0-2117/2404920, filed Jan. 10, 2013.
Authors Unknown, "Crystalline Form of 4-[(5S)-5-(aminomethyl)-2-oxo-1,3-oxazoladin-3-yl]phenyl]morpholin-3-one hydrochloride and crystalline form of S-enantiomer and of racemic 5-Chloro-N-([2-oxo-3-[4-(3-oxo-4-morpholinyl) phynyl]-1,3-oxazolidin-5yl)methyl)-2-thiophene caboxamide", IP.com No. IPCOM00198340D, (Aug. 5, 2010).
Canadian Office Action issued Sep. 16, 2013 in Canadian Application No. 2,788,755, pp. 1-3.
Written Opinion and International Search Report issued May 12, 2011 in PCT/EP2011/051920, pp. 1-4.
Kitchin J, et. al., Synthesis and Structure—Activity Relationships of a Series of Penicillin Derived HIV Proteinase Inhibitors: Heterocyclic Ring Systems Containing P1' and P2' Substituents, J. Med. Chem. (1994), vol. 37, pp. 3707-3716.
International Preliminary Report on Patentability mailed Feb. 10, 2012 in n PCT/EP2011/051920, pp. 1-8.

*Primary Examiner* — Rebecca Anderson
(74) *Attorney, Agent, or Firm* — Jeffrey S. Melcher; Manelli Selter PLLC

(57) ABSTRACT

Provided are a crystalline dihydrate of Rivaroxaban, processes for the preparation thereof, pharmaceutical compositions containing the crystalline dihydrate and processes for preparing and storing the pharmaceutical compositions. Also provided are a crystalline formic acid solvate of Rivaroxaban, processes for the preparation of crystalline Rivaroxaban formic acid solvate and the use of the Rivaroxaban formic acid solvate in the manufacture of the crystalline dihydrate of Rivaroxaban.

11 Claims, 6 Drawing Sheets

DSC (lower curve; left ordinate), and TGA (upper curve; right ordinate) curves of formic acid solvate of Rivaroxaban Powder X-ray diffractogram of Rivaroxaban dihydrate.

IR-spectrum of Rivaroxaban dihydrate.

DSC (lower curve; left ordinate), and TGA (upper curve; right ordinate) curves of Rivaroxaban dihydrate.

CRYSTALLINE FORM OF RIVAROXABAN DIHYDRATE

FIELD OF THE INVENTION

The present invention relates to a novel crystalline dihydrate of Rivaroxaban, processes for the preparation thereof, pharmaceutical compositions comprising said crystalline dehydrate and to processes for preparing and storing said pharmaceutical compositions. The invention also relates to a crystalline formic acid solvate of Rivaroxaban, processes for the preparation of crystalline Rivaroxaban formic acid solvate and to the use of said Rivaroxaban formic acid solvate in the manufacture of the crystalline dihydrate of Rivaroxaban.

BACKGROUND OF THE INVENTION

Rivaroxaban, 5-Chloro-N-({(5S)-2-oxo-3-[4-(3-oxomorpholin-4-yl]phenyl)-1,3-oxazolidin-5-yl}methyl)thiophene-2-carboxamide, also known as BAY 59-7939 and marketed under the trade name Xarelto®, is a direct factor Xa Inhibitor and as such an antithrombotic agent having the formula:

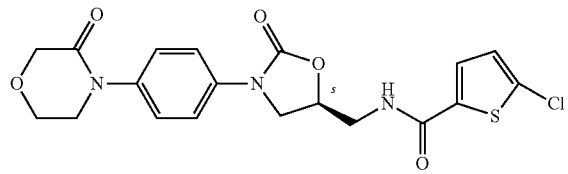 [SMILES: O=C(NC[C@H]1CN(c2ccc(N3CCOCC3=O)cc2)C(=O)O1)c1ccc(Cl)s1]

(see also J. Med. Chem. 2005, 48, 5900-5908).

Rivaroxaban exists in several polymorphic forms, which have been called "modification I", "modification II" and "modification III" in WO 2007/039132. The same document also mentions a hydrate, an NMP solvate, a THF-clathrate and an amorphous form of Rivaroxaban. WO 2007/039132 describes that modification II and the amorphous form are to be preferably used in finished dosage forms due to their higher solubility in comparison to modification I. Modification II is described to have a 4-fold higher solubility compared to modification I.

Form I of Rivaroxabin is reported to be of a relatively low solubility, see e.g. the CHMP assessment report Procedure No. EMEA/H/C/000944, and WO2005/060940 mentions that difficulties in oral bioavailability of Rivaroxaban had allegedly to be overcome during the development of an oral dosage form based on modification I. WO2007/039122 mentions as an alternative that melt extrusion and the use of amorphous Rivaroxaban prepared by melting can be of help in improving the oral bioavailability of Rivaroxaban.

It is interesting to note that the preferred, since more soluble, modification II of Rivaroxaban is not employed in the presently marketed oral dosage forms of Rivaroxaban (see e.g. the CHMP assessment report Procedure No. EMEA/H/C/000944), but the less soluble modification I. One possible explanation might be that modification II of Rivaroxaban can not be easily prepared following the processes disclosed in WO2007/039132, in particular when production of modification II, in particular polymorphically pure modification II, is attempted on commercial scale. In WO2007/039132 modification II is prepared by allowing a solution of Rivaroxaban in 1,4-Dioxan to evaporate at 50° C. or by shock-cooling. These process are not easily carried out on large scale at low cost.

There remains thus a need for a novel polymorph of Rivaroxaban with improved solubility properties compared to the sparsely soluble modification I of Rivaroxaban, which polymorphic form at the same time lends itself to facile production at commercial scale, contrary to modification II, preferably at low cost.

Moreover, different crystal forms of one compound may interconvert, that is under certain conditions one crystal form with favorable characteristics may convert to another crystal form with possibly less favorable characteristics. There is thus a need for pharmaceutical compositions comprising rivaroxaban in that very defined polymorphic state which shows favorable characteristics.

SUMMARY OF THE INVENTION

The present invention relates to a novel crystalline dihydrate of Rivaroxaban having a X-ray powder diffraction pattern comprising peaks at 2-theta angles of 7.1°, 9.8°, 10.6°, 19.7°, 24.2°, and 27.3°+/−0.2°. It relates to processes for the preparation thereof, pharmaceutical compositions comprising said crystalline dihydrate and to processes for preparing and storing said pharmaceutical compositions. The invention also relates to a crystalline formic acid solvate of Rivaroxaban, processes for the preparation of crystalline Rivaroxaban formic acid solvate and to the use of said Rivaroxaban formic acid solvate in the manufacture of the crystalline dihydrate of Rivaroxaban.

DETAILED DESCRIPTION OF THE INVENTION

Figure 4:
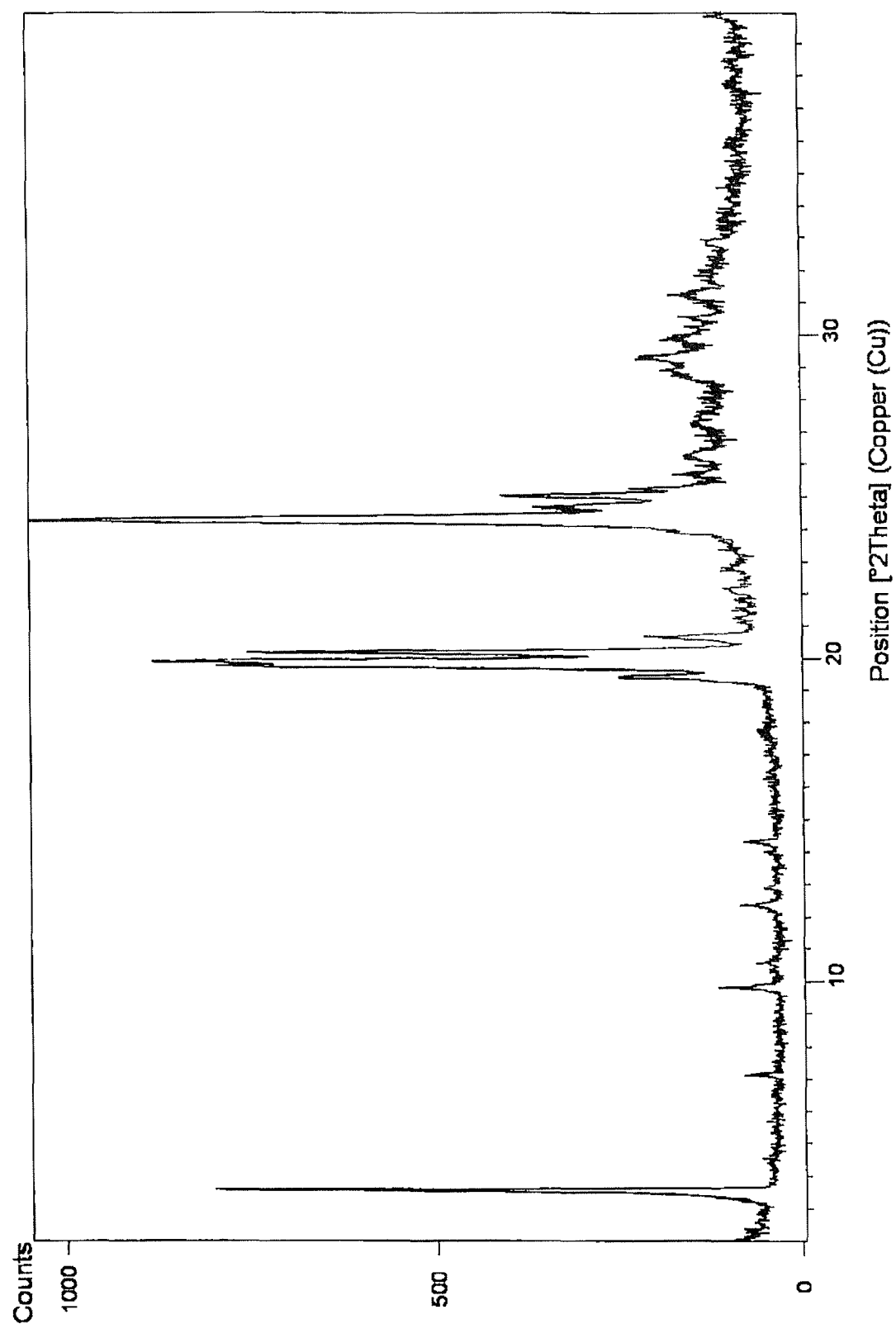
FIG. 4: Powder X-ray diffractogram of Rivaroxaban dihydrate

The present invention relates to a crystalline dihydrate of Rivaroxaban. The crystalline dihydrate of Rivaroxaban can be characterized by an X-ray powder diffraction pattern comprising peaks at 2-theta angles of 7.1°, 9.8°, 10.6°, 19.7°, 24.2°, and 27.3°+/−0.2°, preferably further comprising peaks at 2-theta angles of 20.2°, 25.0° and 29.3°. In particular, the crystalline dihydrate of Rivaroxaban can be characterized by having a PXRD which is substantially in accordance with FIG. 4.

Figure 5:
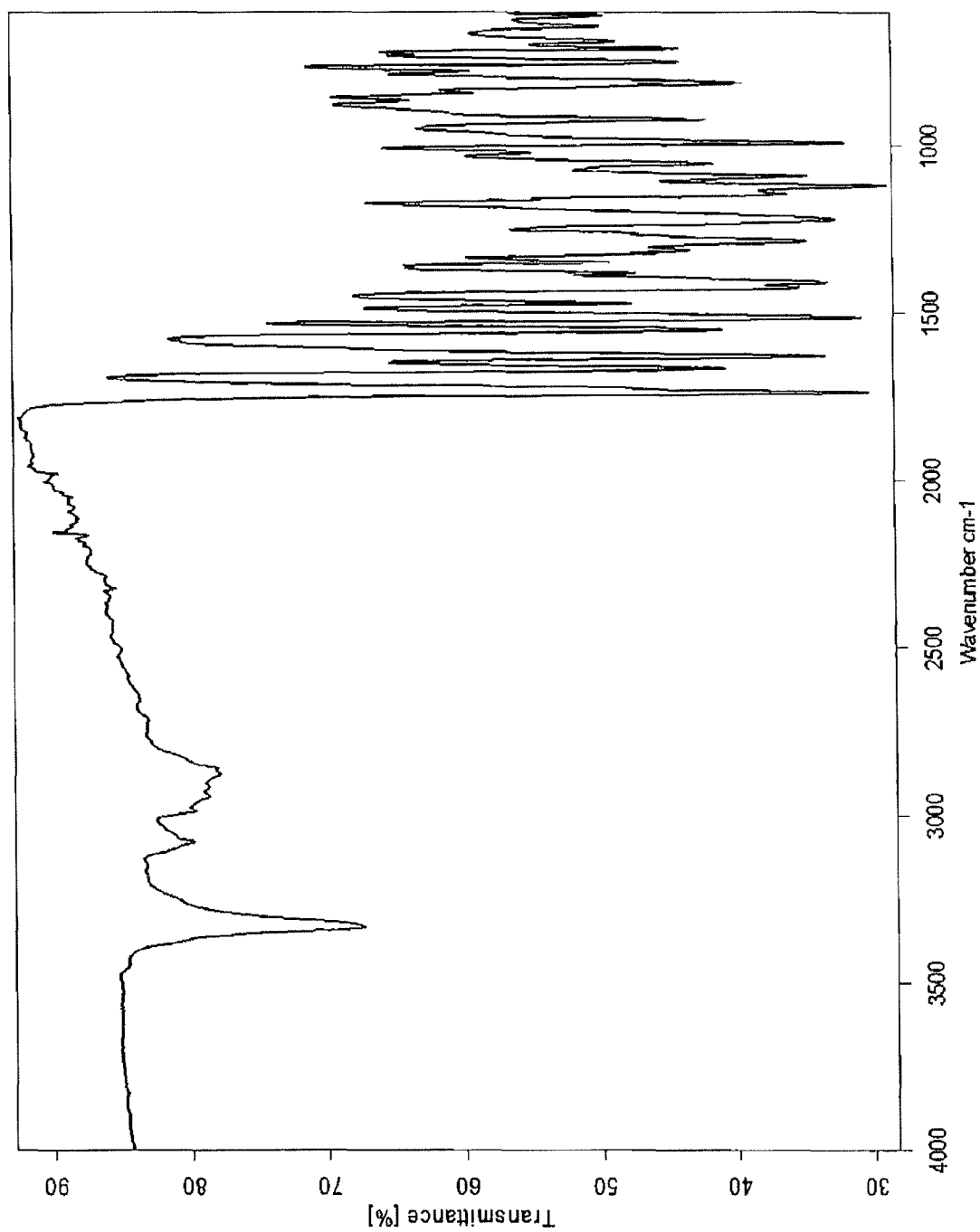
FIG. 5: Infrared-spectrum of Rivaroxaban dihydrate

Alternatively the crystalline dihydrate of Rivaroxaban can be characterized by an infrared spectrum comprising peaks at wavenumbers of about 3335, 1721, 1627, 1515, 1244, 1218, 1023, 922, 864 and 817±2 cm-1. In particular at about 3335, 1737, 1721, 1627, 1515, 1415, 1288, 1244, 1218, 1143, 1023, 991, 922, 864 and 817 cm-1. The typical precision of the peak positions is in the range of ±2 cm-1. In particular the crystalline dihydrate of Rivaroxaban can be described by an Infrared spectrum substantially in accordance with FIG. 5.

Figure 6:
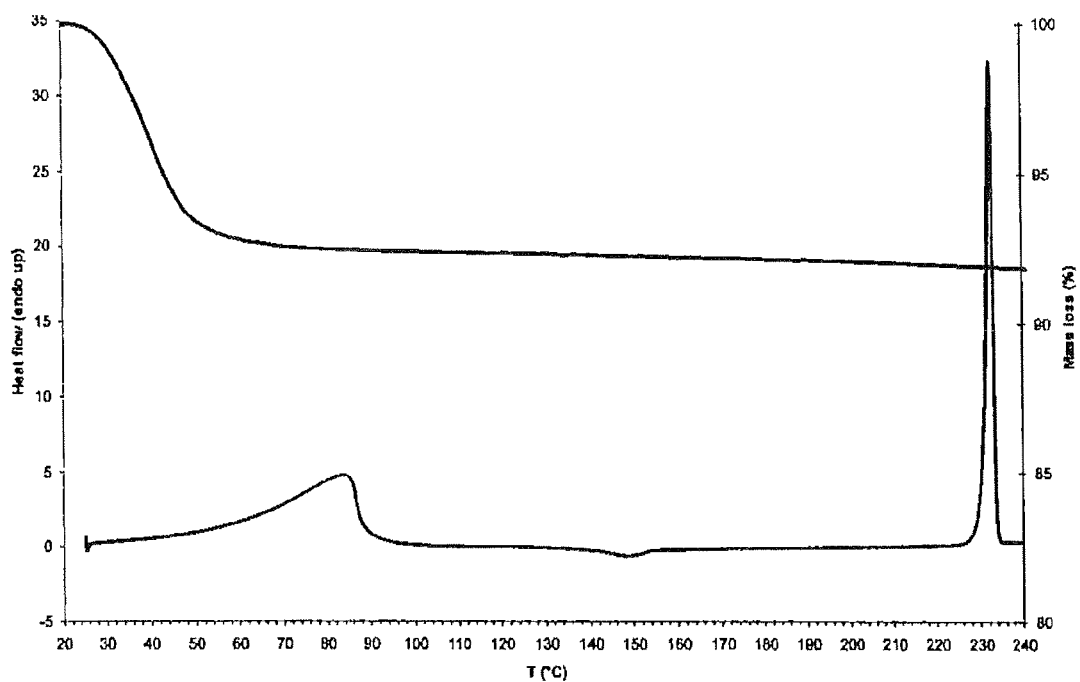
FIG. 6: DSC (lower curve; left ordinate), and TGA (upper curve; right ordinate) curves of Rivaroxaban dihydrate

Alternatively the crystalline dihydrate of Rivaroxaban can be described by having a DSC when measured as set out in the experimental section which is essentially in accordance with FIG. 6.

In contrast to the Rivaroxaban hydrate described in WO 2007/039132, which, according to the TGA curve displayed in the above patent application, contains about 1 mole of water, the novel dihydrate of Rivaroxaban revealed here contains about 2 moles of water. The present invention therefore also relates to a crystalline hydrate of Rivaroxaban containing from 1.6 to 2.4 moles of water per mole of rivaroxaban, more preferably from 1.8 to 2.2 moles of water per mole of rivaroxaban, even more preferably a crystalline dihydrate of Rivaroxaban characterized by a molar ratio rivaroxaban to water of about 1.0 to 2.0.

The present inventors have surprisingly found that the crystalline dihydrate of Rivaroxaban of the present invention shows a 2.5 fold to 3 fold improved solubility compared to form I of Rivaroxaban. Moreover, the present inventors have found a commercially viable process for the preparation of the crystalline dihydrate of Rivaroxaban of the present invention, which is an advantage when compared to the "modification II" of Rivaroxaban. Thus, the present invention enables the commercial production of pharmaceutical compositions of Rivaroxaban with improved bioavailability compared to the commercially available Xarelto® tablets.

The crystalline dihydrate of the present invention is a polymorphically stable compound when stored at the proper conditions, e.g. the dihydrate does not convert to other polymorphic forms at ambient temperature, e.g. when stored at about 25° C. and a relative humidity of about 76% for an extended period of time, e.g. after storage for 6 weeks. The crystalline dihydrate of the present invention is thus appropriate for use in a medicament, such as a pharmaceutical composition.

As described further below, e.g. in FIG. 7, the dihydrate of Rivaroxaban readily converts to an anhydrate form of Rivaroxaban at a relative humidity of about 25%. It is preferred that the crystalline Rivaroxaban dihydrate remain polymorphically stable when used in the context of a pharmaceutical composition. The present invention thus also relates to crystalline Rivaroxaban dihydrate for use in a pharmaceutical composition, preferably for oral administration, wherein the equilibrium relative humidity of said pharmaceutical composition is above 20%.

The present invention also relates to a pharmaceutical composition comprising the crystalline dihydrate of Rivaroxaban of the present invention. The crystalline dihydrate of Rivaroxaban of the present invention may be formulated as tablets, capsules or sachets, in each case according to methods familiar to the person skilled in the art, if appropriate including the addition of further pharmaceutically acceptable excipients.

The pharmaceutical composition comprising the crystalline dihydrate of Rivaroxaban of the present invention may be formulated for oral, parenteral, pulmonal, nasal, sublingual lingual, buccal, rectal, dermal, transdermal, conjunctival or otic administration, as a stent or animplantant. For the preferred oral application, tablets, coated or uncoated, which optionally control release of the drug as desired with rapid release or modified release, or capsules, e.g. soft or hard gelatin capsules, dragees, granules pellets, powder, suspensions or aerosols are possible. Particularly preferred are aqueous suspensions of the crystalline dihydrate of Rivaroxaban of the present invention for oral administration.

Alternatively, a pharmaceutical composition comprising the crystalline dihydrate of Rivaroxaban of the present invention may be for intraveneous, intraarterial, intracardial, intraspinal or intralublar, intramuscular, subcutaneous, intracutaneous, percutaneous or intraperitoneal administration. For the parenteral application injectable preparations, infusions in the form of suspensions or sterile powders are suitable.

A pharmaceutical composition comprising the crystalline dihydrate of Rivaroxaban of the present invention may be prepared by known methods by mixing with inert, non toxic pharmaceutical excipients, e.g. carriers such as microcrystalline cellulose, lactose, mannitol, solvents, e.g. propylenglycols, binders, e.g. polyvinylpyrrolidon, synthetic or natural polymers (e.g., albumin), stabilizers, e.g. antioxidants e.g. ascorbic acid, colorants, e.g., pigments and aromas.

Suitable doses for injectable administration are 0.001 to 1 mg/kg body weight of Rivaroxaban, preferably about 0.02 to 0.5 mg/kg body weight, and for oral administration preferably in the range of about 0.01 to 100 mg/kg body weight, more preferably about 0.01 to 20 mg/kg body weight.

A pharmaceutical composition comprising the crystalline dihydrate of Rivaroxaban of the present invention may be prepared by using a direct formulation process of the crystalline dihydrate of Rivaroxaban or a granulation process of the crystalline dihydrate of the invention including a wet granulation process as disclosed for example in WO 2005/060940. For example, the dihydrate of Rivaroxaban may be formulated also as disclosed e.g. in WO 2006/072367 or WO 2007/039122.

The pharmaceutical composition comprising the crystalline dihydrate of Rivaroxaban of the present invention may also comprise other polymorphic forms of Rivaroxaban, such as "modifications I, II and/or III" described in WO 2007/039132, however, in a preferred embodiment, the present invention relates to a pharmaceutical composition comprising the crystalline dihydrate of Rivaroxaban wherein the equilibrium relative humidity of said pharmaceutical composition is above 20%.

It has now been found that the crystalline dihydrate of Rivaroxaban of the present invention transforms into an anhydrate form of Rivaroxaban when crystalline dihydrate of Rivaroxaban is exposed to conditions with less than 20% relative humidity. Usually about one hour of exposure to low relative humidity is sufficient for this transformation. Such conditions are for example found during pharmaceutical production in countries with a desert climate or during storage of a pharmaceutical composition in such countries without special precautions.

Figure 7:
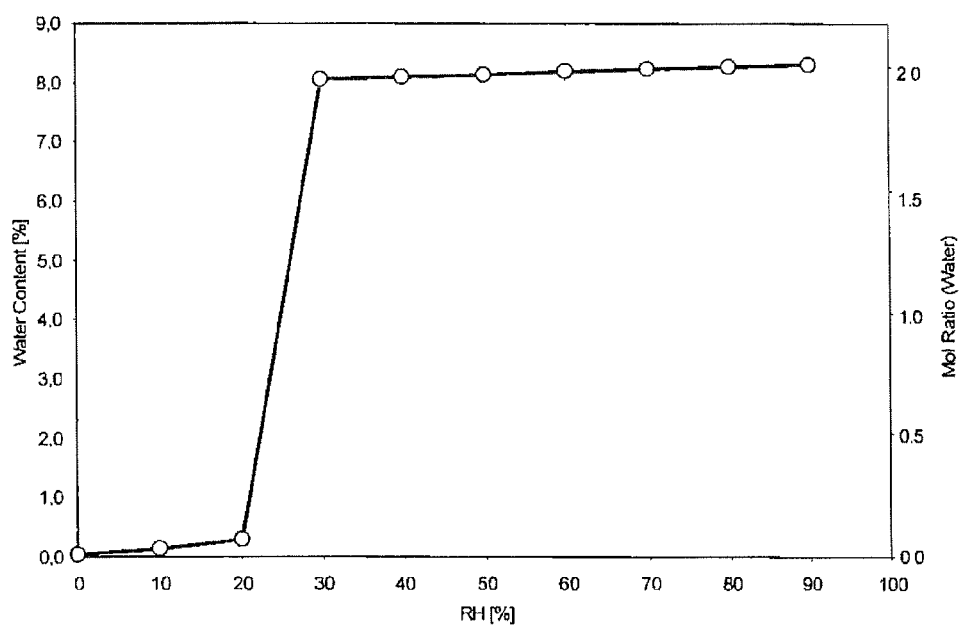
FIG. 7: Moisture desorption diagram of dihydrate of Rivaroxaban

The above described transformation of the crystalline dihydrate of Rivaroxaban of the present invention into a different form can be concluded from FIG. 7 which shows that the mass of a test sample of the crystalline dihydrate of Rivaroxaban of the present invention changes when exposed to decreasing values of relative humidity; in particular, a drastic change in water content is observed at a relative humidity of about 30% to 20%.

The present invention therefore relates to a pharmaceutical composition comprising the crystalline dihydrate of Rivaroxaban wherein more than 90%, more preferably more than 95% of the crystalline dihydrate of Rivaroxaban of the present invention present in said composition is stably present as the crystalline dihydrate of Rivaroxaban of the present invention. The present invention also relates to pharmaceutical compositions comprising crystalline dihydrate of Rivaroxaban wherein the rivaroxaban present in said composition does not show XRPD-peaks at the diffraction angles [2θ(°)] of about 8.9, 17.7, and/or 26.7. In particular, the present invention relates to such pharmaceutical compositions wherein the crystalline dihydrate of Rivaroxaban of the present invention is the only detectable crystalline from of rivaroxaban in said pharmaceutical composition.

"Stably present" as defined herein means that even after storage of the pharmaceutical composition for 180 days, and preferably even after storage for two years, the crystalline dihydrate of Rivaroxaban initially comprised in the pharmaceutical composition is still present as crystalline dihydrate of Rivaroxaban after storage for the indicated period. Such compositions can be produced by avoiding arid conditions, such as low relative humidity of the air, during the formulation steps. Furthermore, the above-identified dry conditions are to be avoided during storage in order to preserve the pharmaceutical composition of the invention in its desired state.

In a preferred embodiment the pharmaceutical composition of the invention comprises the crystalline dihydrate of Rivaroxaban as the only detectable form of rivaroxaban. Analysis of the polymorphic state of rivaroxaban in a pharmaceutical composition can be performed by any suitable method known in the art, for example by XRPD.

It is preferred that the pharmaceutical composition of the invention exhibits an equilibrium relative humidity of above 20%, preferably of from 25% to 100%, more preferably of from 30% to 80%, such as from 35% to 80%, in particular from 40% to 75% or from 35% to 70%, for at least 180 days, preferably for at least two years.

The equilibrium relative humidity of the pharmaceutical compositions or of crystalline dihydrate of Rivaroxaban as herein described is measured by determining the relative humidity in % in the air above a test sample, e.g. a pharmaceutical composition of the invention, after establishment of a humidity equilibrium in a closed system at a constant temperature according to the following method: the equipment used is the commercially available measuring chamber Rotronic AW-VC comprising a hygrometer of the type BT-RS1. The test sample, e.g. a pharmaceutical composition of the invention, is filled into a sampling dish which is placed into the measuring chamber which has been thermostated to a temperature of 25+/−1° C., said chamber is subsequently closed and sealed. After establishment of an equilibrium of the relative humidity which state is typically shown by the disappearance of a trend indication, the value of the relative humidity in % is read from the hygrometer. Relative humidity is defined as the equilibrium relative humidity of the pharmaceutical compositions as measured as herein described. Filling of the chamber is to be performed in such a way as to provide complete filling of said chamber according to the instructions of the manufacturers. In case the test sample is a powder or granules for oral suspension, or a liquid suspension, said sample is directly placed into the above mentioned sampling dish. In case the test sample is a capsule, the appropriate number of capsules are opened and their contents is filled into the sampling dish. In case the test sample is a tablet, the appropriate number of tablets is crushed by using a mortar, and filled into the sampling dish. In cases where the equilibrium humidity is expected to be below 20%, the above described preparation of the test samples before measurement and the measurement itself as herein described is to be performed in a glove box being equipped with a hygrometer wherein a relative humidity of about 5% is to be established by e.g. flushing with dried air or nitrogen. The above described method for measurement of the equilibrium relative humidity of the pharmaceutical compositions of the invention is herein also called ERH method.

The pharmaceutical composition of the present invention is preferably stored in a not too dry environment, and preferably it is to be assured that the storage environment remains not too dry during the lifetime of the pharmaceutical composition.

The invention therefore also relates to a container comprising a pharmaceutical composition of the invention, which container is capable to keep the equilibrium relative humidity of the composition at above 20%, preferably of from 25% to 100%, more preferably of from 30% to 80%, such as from 35% to 80%, in particular from 40% to 75% or from 35% to 70%, for at least 180 days, preferably for at least two years. This can be achieved, for example, by use of a refrigerator with a means to humidify the interior atmosphere, or by equipping a container with a means to keep the composition relatively humid, such as a saturated solution of sodium bromide or potassium carbonate in water.

The products or intermediate products obtained in the various steps of herein described processes are preferably stored at an environmental relative humidity of above 20%. Said products may thus be stored in moisture-tolerant storage material, such as aluminium barrels or drums, in so-called Nirosta® drums, such as commercially available as Müller® drums, as long as storage is in a room or container wherein the relative humidity can be controlled to a value of above 20%, more preferably above 30%, for example by addition of one of the above-mentioned means.

The pharmaceutical compositions of the invention are preferably packaged or filled into primary packaging material at an environmental relative humidity of from 25% to 100%, more preferably of from 30% to 80%, such as from 35% to 80%, in particular from 40% to 75% or from 35% to 70%. In one aspect, the primary packaging material can be chosen to be water-impermeable, such as an aluminum-aluminum-blister or PVC/CTFE-blisters (Polyvinylidenechloride/Chlorotrifluoroethylene), thus keeping the equilibrium relative humidity of the pharmaceutical composition at the desired moisture.

Alternatively, the primary packaging material containing the pharmaceutical composition of the present invention may have a higher water-permeability, such as PVC, PET (polyester) or PS (polystyrene), and is then preferably stored under controlled conditions as described above, in order to achieve stable storage of the pharmaceutical compositions of the invention, for example at room temperature, such as at a temperature of about 20° C. to 30° C., e.g. at about 25° C., for a prolonged period, e.g. for at least 6 months, preferably at least about 24 months, e.g. for up to at least 24 months, e.g. for up to at least about 30 months, such as for up to about 60 months, and at an environmental relative humidity of from 25% to 100%, more preferably of from 30% to 80%, such as from 35% to 80%, in particular from 40% to 75% or from 35% to 70%.

A preferred primary packaging material is a bottle, e.g. a glass or plastic bottle, e.g. a polyethylene bottles, such as known as securitainer, having e.g. a screw closure, or is a blister, e.g. an aluminium blister or strip, e.g. a blister consisting of 2 aluminium foils or strips, or a blister comprising an Aclar® foil and an aluminium cover foil, or may be any other suitable container. More preferably said container is a gas-tight container, such as an air-tight container.

The primary packaging material containing the pharmaceutical composition of the invention is obtained by filling the pharmaceutical compositions of the invention into said primary packaging material under the conditions as hereinabove described.

This knowledge about storage conditions is particularly useful, if the pharmaceutical composition is intended to be used in a country with a very dry climate, such as a desert climate. The present invention therefore also relates to a pharmaceutical composition comprising the crystalline dihydrate of Rivaroxaban for use in a country comprising areas with a BWh or BWk climate according to the Köppen-Geiger climate classification, wherein the equilibrium relative humidity of the pharmaceutical composition is above 20%, preferably of from 25% to 100%, more preferably of from 30% to 80%, such as from 35% to 80%, in particular from 40% to 75% or from 35% to 70%, for at least 180 days, preferably for at least two years, and to the use of a primary packaging material or a combination of a primary packaging material with a container which is capable to keep the equilibrium relative humidity of the pharmaceutical composition at above 20%, preferably of from 25% to 100%, more preferably of from 30% to 80%, such as from 35% to 80%, in particular from 40% to 75% or from 35% to 70%, for at least 180 days, preferably for at least two years, for storage of a pharmaceutical composition comprising the crystalline dihydrate of Rivaroxaban for use in a country comprising areas with a BWh or BWk climate according to the Köppen-Geiger climate classification.

As mentioned above, special care as to the relative environmental humidity and as to the equilibrium relative humidity of the composition should preferably be taken during the production of pharmaceutical compositions of the invention.

Therefore, the present invention also relates to a process for preparing a pharmaceutical composition of the invention comprising the steps of
a) mixing the crystalline dihydrate of Rivaroxaban of the invention with one or more pharmaceutically acceptable excipients at a relative humidity of above 20%;
b) optionally granulating the mixture obtained in step a) at a relative humidity of above 20%; and
c) further processing the mixture obtained in step a) or the granulate obtained in step b) at a relative humidity of from 25% to 100%, more preferably of from 30% to 80%, such as from 35% to 80%, in particular from 40% to 75% or from 35% to 70%, to obtain a preferred pharmaceutical composition of the invention.

The mixture obtained from step a) or the granulate obtained from step b) as described above is preferably processed into an oral dosage form, like a capsule or a tablet, or granules for oral suspension, or a powder for oral suspension.

In a preferred embodiment, the obtained pharmaceutical composition having an equilibrium relative humidity of above 20%, such as from 25% to 100%, more preferably of from 30% to 80%, such as from 35% to 80%, in particular from 40% to 75% or from 35% to 70%, is filled into a primary packaging material and the stored in a container capable of maintaining the equilibrium relative humidity of the pharmaceutical composition at above 20%, for example from 25% to 100%, more preferably of from 30% to 80%, such as from 35% to 80%, in particular from 40% to 75% or from 35% to 70%, for at least 6 months.

As explained above, proper storage conditions for the preferred pharmaceutical compositions of the invention are important for maintaining the compositions in the desired preferred form. Thus, the present invention further relates to the use of a container capable of maintaining a gaseous atmosphere at a relative humidity of above 20%, such as from 25% to 100%, more preferably of from 30% to 80%, such as from 35% to 80%, in particular from 40% to 75% or from 35% to 70%, for at least 6 months for storage of a preferred pharmaceutical composition of the invention. Further, the present invention relates to the use of a gaseous atmosphere having a relative humidity of above 20%, such as from 25% to 100%, more preferably of from 30% to 80%, such as from 35% to 80%, in particular from 40% to 75% or from 35% to 70% to stabilize the crystalline dihydrate form of rivaroxaban.

As explained above, the present inventors have found a commercially viable process for the preparation of the crystalline dihydrate of Rivaroxaban of the present invention, which is an advantage when compared to the "modification II" of Rivaroxaban. A novel crystalline formic acid solvate is a useful intermediate in said process.

Figure 1:
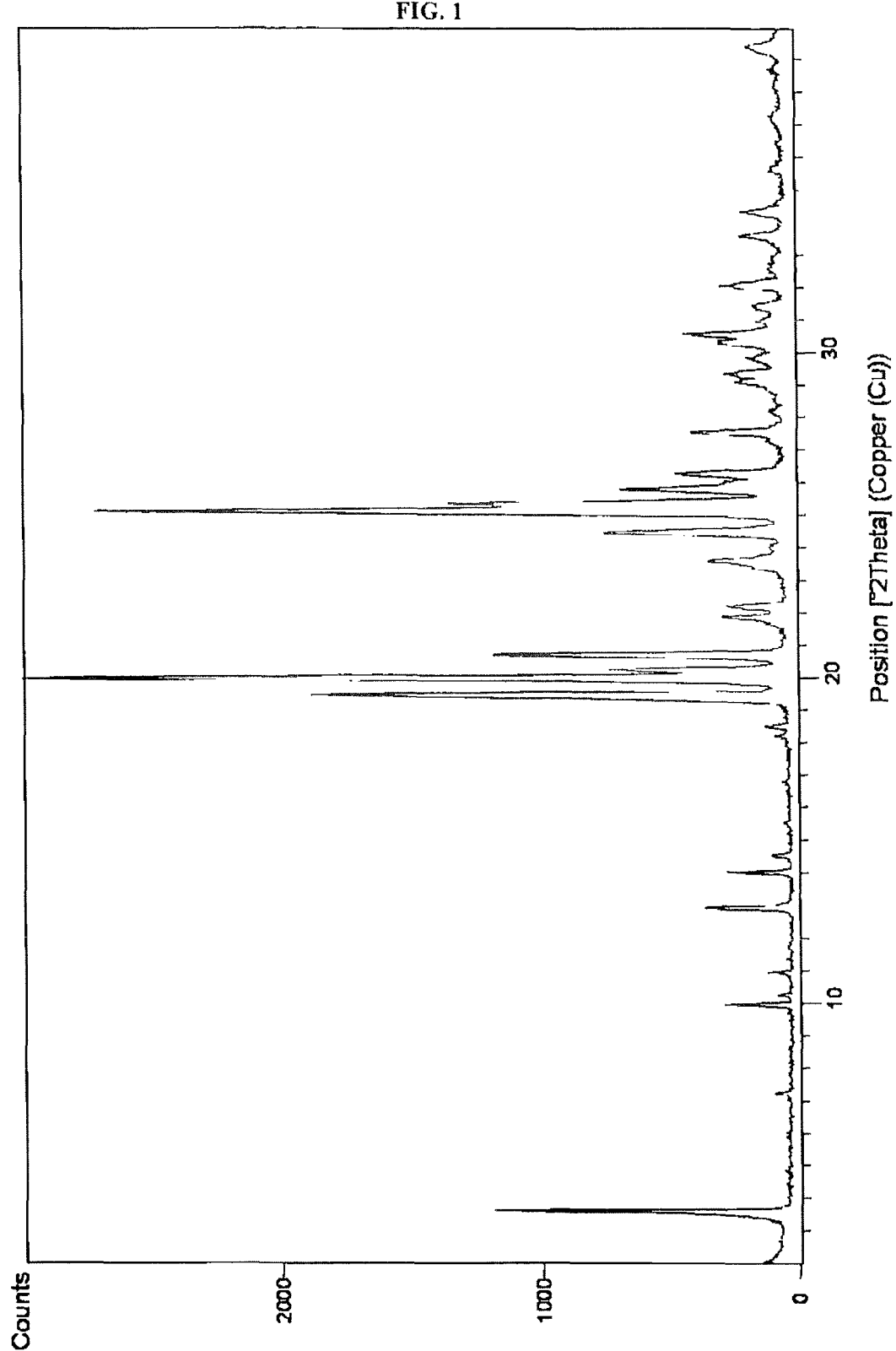
FIG. 1: Powder X-ray diffractogram of formic acid solvate of Rivaroxaban

The present invention therefore also relates to a crystalline formic acid solvate of Rivaroxaban having a X-ray powder diffraction pattern comprising peaks at 2-theta angles of 3.6°, 9.9°, 12.9°, 19.4°, 20.0°, 20.7°, 25.1° and 27.5°±0.2°, preferably further comprising peaks at 14.0°, 21.9°, and 24.4°. °. In particular, the formic acid solvate of Rivaroxaban can be characterized by having a PXRD which is substantially in accordance with FIG. 1.

Figure 2:
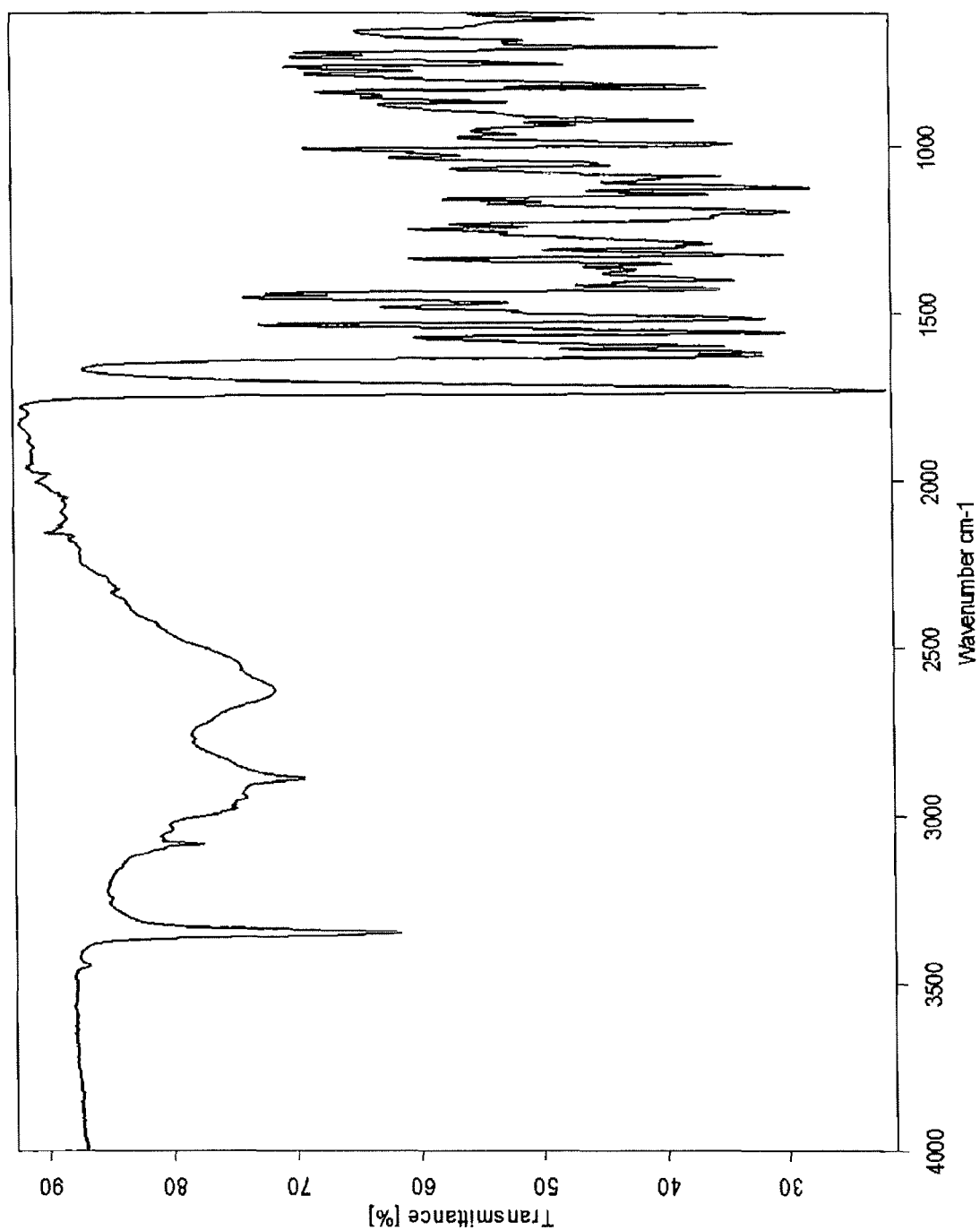
FIG. 2: Infrared-spectrum of formic acid solvate of Rivaroxaban

Alternatively the crystalline formic acid solvate of Rivaroxaban can be characterized by having an attenuated total reflectance infrared spectrum comprising absorption bands at wavenumbers of about 3350, 2890, 1729, 1614, 1597, 1324, 1193, 1122, 992, 827, 814, and 703 cm-1±2 cm-1. The typical precision of the peak positions is in the range of ±2 cm-1. In particular the crystalline formic acid solvate of Rivaroxaban can be described by an Infrared spectrum substantially in accordance with FIG. 2.

Figure 3:
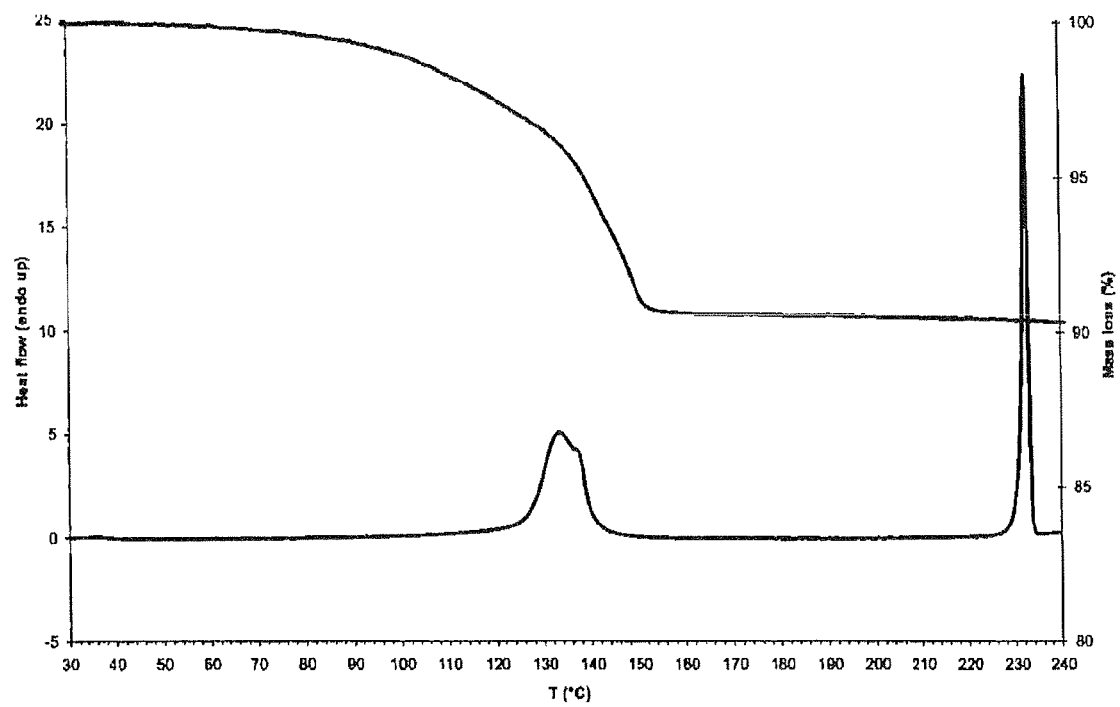
FIG. 3: DSC (lower curve; left ordinate), and TGA (upper curve; right ordinate) curves of formic acid solvate of Rivaroxaban

Alternatively the crystalline formic acid solvate of Rivaroxaban can be described by having a DSC and/or TGA when measured as set out in the experimental section which is essentially in accordance with FIG. 3. The crystalline formic acid solvate of Rivaroxaban contains about 0.9 to 1.1 mol formic acid. Approximately 1 mol of HCOOH is lost when performing a TGA.

The crystalline formic acid solvate of Rivaroxaban readily crystallizes out of formic acid and yields Rivaroxaban in high purity and high yield—important features for a key intermediate to be employed in an industrial process.

The present invention therefore also relates to a process for the preparation of crystalline Rivaroxaban formic acid solvate, comprising the step of crystallizing Rivaroxaban from formic acid. The crystalline formic acid solvate of Rivaroxaban can be prepared by contacting Rivaroxaban with formic acid. Suitable starting material is any polymorph of Rivaroxaban or Rivaroxaban in amorphous form.

Alternatively Rivaroxaban formic acid solvate may be isolated when starting from the last step of chemical synthesis, e.g. following the synthesis methods disclosed in WO 2004/060887 or WO 2005/068456, optionally after removing the solvents used in the synthesis, e.g. by evaporation, by crystallization from formic acid.

Typically Rivaroxaban is suspended in formic acid or a mixture of formic acid and water optionally in the presence of an organic solvent, e.g. a ketone, e.g. acetone, methylethylketone or methylisobutylketone or a nitril, e.g. acetonitril. The mixture is optionally heated to induce dissolution followed by cooling of the solution to induce or complete crystallization.

The amount of formic acid to produce the crystalline formic acid solvate is at least one equivalent of formic acid to about 5 to 10 equivalents or more compared to Rivaroxaban when prepared in presence of organic solvents. Alternatively formic acid neat may be used to form the crystalline formic acid solvate of Rivaroxaban.

Preferably crystallization of Rivaroxaban formic acid solvate is performed at ambient temperature, e.g. at about 30° C. to about 15° C. and is not critical. To complete crystallization the obtained suspension may be cooled to about 0° C. to 5° C., e.g. in an ice bath or fridge.

Isolation and drying of the crystalline formic acid solvate may be performed by conventional methods, e.g. filtration or centrifugation. The crystalline formic acid solvate of Rivaroxaban may be washed using organic solvents, e.g. the organic solvents disclosed above, or formic acid or mixtures thereof. Preferred methods of preparing the crystalline formic acid solvate of Rivaroxaban is performing the crystallization in neat formic acid or by crystallization from a formic acid/ acetonitril mixture.

The formic acid solvate of Rivaroxaban is stable when stored at low relative humidity, e.g. less than about 20% relative humidity at 25° C. However when stored at a relative humidity of more than 20%, e.g. at 30%, 60% or 97% relative humidity formic acid is lost and the dihydrate of Rivaroxaban is formed. Also, when suspending the crystalline formic acid solvate of Rivaroxaban in aqueous medium, pure dihydrate of Rivaroxaban is formed.

The present invention therefore also relates to a process of preparing the crystalline dihydrate of Rivaroxaban of the invention from the formic acid solvate of Rivaroxaban, said process comprising the step of contacting the formic acid solvate of Rivaroxaban with an amount of water sufficient to cause transformation to the crystalline dihydrate. In particular, a) the formic acid solvate of Rivaroxaban is first suspended in water;
b) then optionally the pH is adjusted to a value of 3 to 10, more preferably to a value of 5 to 9, by addition of a suitable amount of base, such as an alkali metal hydroxide; and then
c) sufficient time for transformation to the crystalline dihydrate of Rivaroxaban is allowed; and then
d) the crystalline dihydrate of Rivaroxaban of the present invention is isolated.

In one example the formic acid solvate of Rivaroxaban is suspended at room temperature in water, e.g. with stirring, upon which transformation of the formic acid solvate of Rivaroxaban to the dihydrate of Rivaroxaban takes place.

In preferred embodiments, Rivaroxaban is suspended in water at ambient temperature, e.g. about 20° C. to 25° C. and the mixture is stirred for the time sufficient to complete conversion of the formic acid solvate of Rivaroxaban to the dihydrate. The concentration of Rivaroxaban to water is typically from about 1:10 (g/vol) to 1:100 (g/vol), typically a 10% to 50% suspension (g Rivaroxaban formic acid solvate:ml of water) is used.

Stirring is preferably performed in the transformation step. The suspension is stirred for e.g. 30 min to several days, e.g. for 3 to 24 hours, e.g. from 5 to 16 h to complete the desired conversion.

Optionally the pH of the suspension may be adjusted to a pH wherein the formic acid is present partially or completely as salt, e.g. to a pH of about 3 to 10, e.g., to about 4 to 8, e.g. to about 5 to 7 using a base.

The base is not critical and may be selected from an alkali hydroxide, e.g. sodium hydroxide or potassium hydroxide, from an alkali carbonate or hydrogen carbonate, e.g. sodium carbonate or sodium bicarbonate or an amine base, e.g. ammonia, e.g. aqueous ammonia. It is advantageous to grind the formic acid solvate of Rivaroxaban before performing the transformation step.

After completion of the transformation the dihydrate of Rivaroxaban may be isolated by conventional methods, e.g. filtration or centrifugation.

The formic acid solvate of Rivaroxaban is thus a useful intermediate for the preparation of the crystalline dihydrate of the invention. The present invention therefore also relates to the use of Rivaroxaban formic acid solvate in the manufacture of the crystalline dihydrate of Rivaroxaban of the invention.

The present invention is further illustrated by the following examples, which are not to be construed to be in any way limiting to the present invention.

EXPERIMENTAL

The X-ray powder diffraction patterns (XRPD) were obtained with a X'Pert PRO diffractometer (PANalytical, Almelo, The Netherlands) equipped with a theta/theta coupled goniometer in transmission geometry, programmable XYZ stage with well plate holder, Cu—K$\alpha$1,2 radiation source (wavelength 0.15419 nm) with a focussing mirror, a 0.5° divergence slit and a 0.02° soller slit collimator on the incident beam side, a 2 mm anti-scattering slit and a 0.02° soller slit collimator on the diffracted beam side and a solid state PIXcel detector. The patterns were recorded at a tube voltage of 40 kV, tube current of 40 mA, applying a step size of 0.01° 2-theta with 80 s per step in the angular range of 2° to 40° 2-theta.

Infrared spectra (IR) were collected on a MKII Golden Gate™ Single Reflection Diamond ATR (attenuated total reflection) cell with a Bruker Tensor 27 FTIR spectrometer with 4 cm-1 resolution at ambient conditions. To collect a spectrum a spatula tip of a sample was applied to the surface of the diamond in powder form. Then the sample was pressed onto the diamond with a sapphire anvil and the spectrum was recorded. A spectrum of the clean diamond was used as background spectrum. A typical precision of the wavenumber values is in the range of about ±2 cm-1. Thus, an infrared peak that appears at 1716 cm-1 can appear between 1714 and 1718 cm-1 on most infrared spectrometers under standard conditions.

The moisture desorption isotherm were recorded with a SPS-11 moisture sorption analyzer (MD Messtechnik, Ulm, and D). The measurement cycle was performed by a decrease relative humidity (RH) in 10% steps. The equilibrium condition for each step was set to a mass constancy of ±0.001% over 50 min. The temperature was 25° C.±01° C. TGA of the crystalline dihydrate revealed a weight loss of 2 moles of water.

Thermo gravimetric analysis was performed with the thermo gravimetric system TGA-7 using the Pyris Software for Windows NT (Perkin-Elmer, Norwalk, Conn., USA), 50 µl platinum pans, nitrogen purge gas (sample purge: 20 ml min-1, balance purge: 40 ml min-1).

Differential scanning calorimetry (DSC) was performed with a DSC 7 (Perkin-Elmer, Norwalk, Conn., USA) using the Pyris software. A sample of about 4 mg was weighed into a 25 µl Al-pan. Dry nitrogen was used as the purge gas (purge: 20 ml min-1).

Example 1

Rivaroxaban.Formic Acid Solvate 2 g of Rivaroxaban (form I) were suspended in 13 g of formic acid. The mixture was heated in a water bath to a temperature of about 55° C. A Solution was obtained. 55 g of acetonitril were added and the mixture was allowed to cool to ambient temperature. The suspension was then stored in the fridge (+4° C.) overnight. The crystals were isolated by filtration and then dried in vacuo (approx. 20 mbar) overnight. Yield 1.65 g Example 2

Rivaroxaban.Formic Acid Solvate 6.38 g of Rivaroxaban (form I) were suspended in 44 g of formic acid. The mixture was heated in a water bath to a temperature of about 55° C. A Solution was obtained. The solution the allowed to cool to ambient temperature. The suspension was then stirred for one hour at ambient temperature and then cooled in an ice bath to 0° C. After stirring for two hours at 0° C. the crystals were isolated by filtration, washed with 5 mL of cold formic acid and then dried in vacuo (approx. 20 mbar) at ambient temperature overnight. Yield 4.82 g Example 3

Rivaroxaban Dihydrate 0.5 g of Rivaroxaban.Formic acid crystals were suspended in water and stirred for approx. one hour at room temperature. To the obtained suspension 1.25 ml (1.2 equivalents) of a 1 molar aqueous sodium hydroxide solution were added and the mixture was stirred for 16 hours at room temperature. After filtration the solid was washed with water and sucked dry for approx. 15 minutes. The product Rivaroxaban Dihydrate was obtained as a colorless wet crystalline solid.

Example 4

Stability of Rivaroxaban Dihydrate 0.10 g of Rivaroxaban dihydrate were stored at 25° C.±2° C. for 6 weeks in an atmosphere of about 70% and the sample was analyzed by infrared spectroscopy after 6 weeks. Rivaroxaban Dihydrate was polymorphic stable at 25° C.±2° C. at a relative humidity of about 76% for at least 6 weeks.

The invention claimed is:

1. Crystalline dihydrate of Rivaroxaban having a X-ray powder diffraction pattern comprising peaks at 2-theta angles of 7.1°, 9.8°, 10.6°, 19.7°, 24.2°, and 27.3°+/−0.2°.

2. Crystalline dihydrate of Rivaroxaban according to claim 1, having an attenuated total reflectance infrared spectrum comprising absorption bands at 3335, 1721, 1627, 1515, 1244, 1218, 1023, 922, 864 and 817±2 cm-1.

3. Pharmaceutical composition comprising crystalline dihydrate of Rivaroxaban according to claim 1.

4. The pharmaceutical composition of claim 3, wherein more than 90% of the Rivaroxaban is stably present as the crystalline dihydrate of Rivaroxaban.

5. A process for preparing a pharmaceutical composition according to claim 3 comprising the steps of
   a) mixing crystalline dihydrate of Rivaroxaban having a X-ray powder diffraction pattern comprising peaks at 2-theta angles of 7.1°, 9.8°, 10.6°, 19.7°, 24.2°, and 27.3°+/−0.2° with one or more pharmaceutically acceptable excipients at a relative humidity of above 20%;
   b) optionally granulating the mixture obtained in step a) at a relative humidity of above 20%; and
   c) further processing the mixture obtained in step a) or the granulate obtained in step b) at a relative humidity of above 20% to obtain a pharmaceutical composition according to claim 3.

6. The process of claim 5 wherein the mixture or granulate is processed into an oral dosage form.

7. The process of claim 5 comprising the additional step of filling the obtained pharmaceutical composition having an equilibrium relative humidity of above about 20% into a container capable of maintaining the equilibrium relative humidity of the pharmaceutical composition at above 20% for at least 6 months.

8. Pharmaceutical composition comprising crystalline dihydrate of Rivaroxaban according to claim 3, wherein the equilibrium relative humidity of said pharmaceutical composition is above 20%.

9. The pharmaceutical composition of claim 4, wherein more than 95% of the Rivaroxaban is present as the crystalline dihydrate of Rivaroxaban.

10. The process of claim 6 wherein the mixture or granulate is processed into an aqueous oral suspension.

11. Crystalline dihydrate of Rivaroxaban according to claim 1, further comprising peaks at 2-theta angles of 20.2°, 25.0° and 29.3°.

* * * * *